United States Patent
Castelijns

(10) Patent No.: US 9,334,224 B2
(45) Date of Patent: May 10, 2016

(54) PROCESS TO PRODUCE ALKENOIC ACID ESTERS FROM LACTONES

(71) Applicant: DSM IP ASSETS B.V., Heerlen (NL)

(72) Inventor: Anna Maria Cornelia Francisca Castelijns, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 587 days.

(21) Appl. No.: 13/624,851

(22) Filed: Sep. 21, 2012

(65) Prior Publication Data

US 2013/0079548 A1 Mar. 28, 2013

Related U.S. Application Data

(60) Provisional application No. 61/538,423, filed on Sep. 23, 2011.

(30) Foreign Application Priority Data

Sep. 23, 2011 (EP) ..................................... 11182459

(51) Int. Cl.
*C07C 67/00* (2006.01)
*C07C 51/09* (2006.01)
*C07C 67/36* (2006.01)
*C07C 67/03* (2006.01)

(52) U.S. Cl.
CPC ...................... *C07C 67/03* (2013.01)

(58) Field of Classification Search
USPC .................. 560/204, 211; 562/590
See application file for complete search history.

(56) References Cited

U.S. PATENT DOCUMENTS

| | | | | |
|---|---|---|---|---|
| 3,065,263 A | * | 11/1962 | Carlson | 562/515 |
| 4,740,613 A | * | 4/1988 | Fischer et al. | 560/205 |
| 5,144,061 A | | 9/1992 | Hoelderich et al. | |

FOREIGN PATENT DOCUMENTS

| | | | |
|---|---|---|---|
| EP | 0238002 A1 | | 9/1987 |
| WO | WO01/68583 | * | 3/2001 |

OTHER PUBLICATIONS

Li, L., Yoshinga, Y., Okuhara, T. Unprecedented accerlation effects of water on acid-catalyzed reactions over molybdena-zirconia catalysts, Catalysis Letters, vol. 83, Nos. 3-4, Nov. 2002.*
Manzer, L.E., Catalytic synthesis of alpha-methylene-gama-valerolactone: a biomass-derived acrylic monomer, Applied Catalysis A: General, 272 (2004) 249-256.*
Extended European Search Report of EP11182459.5 Completion Date: Nov. 17, 2011.
Virta, Zeolites, U.S. Geological Survey Minerals Yearbook (1999) at 84.1-84.4.

* cited by examiner

*Primary Examiner* — Paul A Zucker
*Assistant Examiner* — Mark Luderer
(74) *Attorney, Agent, or Firm* — Miles & Stockbridge, PC

(57) ABSTRACT

This invention relates to a process for the preparation of alkenoic acid esters comprising contacting a lactone with an alcohol and an acidic catalyst in the gas phase, characterized in that the process is carried out in the presence of at least 0.26 wt. % water, relative to the amount of the lactone. The process may result in a good production yield and selectivity with respect to the production of alkenoic acid esters and may also result in less formation of dialkylethers. The improved yield advantageously allows energy conservation.

16 Claims, No Drawings

PROCESS TO PRODUCE ALKENOIC ACID ESTERS FROM LACTONES

CROSS REFERENCE TO RELATED APPLICATIONS

This application claims priority to European Application No. 11182459.5, filed Sep. 23, 2011, and U.S. Provisional Application No. 61/538,423, filed Sep. 23, 2011, the content of both of which are incorporated herein by reference in their entireties.

BACKGROUND

1. Field of the Invention

The present invention relates to a process for the production of alkenoic acid esters from lactones.

2. Description of Related Art

The present invention relates to a process for the preparation of alkenoic acid esters comprising contacting a lactone with an alcohol and an acidic catalyst in the gas phase. Such a process is known in the art and is described e.g. in U.S. Pat. No. 5,144,061 and U.S. Pat. No. 4,740,613. The catalysts used or suggested in the process of U.S. Pat. No. 5,144,061 are acidic zeolites or phosphates. The catalysts used or suggested in the process of U.S. Pat. No. 4,740,613 are acidic zeolites, acidic oxides of group III or IV and subgroups IV and VI of the periodic table, such as silica in the form of silica gel, kieselguhr or quartz, as well as titanium dioxide, phosphorus pentoxide, alumina, molybdenum oxides.

SUMMARY

The inventors have found that a problem of a process for the preparation of alkenoic acid esters comprising contacting a lactone with an alcohol and an acidic catalyst in the gas phase as described in U.S. Pat. No. 5,144,061 and U.S. Pat. No. 4,740,613 is that the production of dialkyl ethers is high. The alcohol which is present in the reaction mixture is essential for the preparation of alkenoic acid esters but can also react with itself to form dialkylethers. For example if the alcohol is methanol, dimethylether can be formed.

The extent of production of dialkyl ethers can be expressed for example as the selectivity towards formation of dialkylethers based on the amount of alkanol which is converted in the process. Ideally this selectivity is zero but in practice the inventors found that the selectivity towards the formation of dialkylethers is often much higher.

The formation of dialkyl ethers is undesired because it may result in suboptimal use of the substrate lactone and also because the dialkyl ethers have to be separated from the product alkenoic acid esters and because a (substantial) part of the alkanol is converted into the undesired ether which means higher costs.

It is therefore an aim of the invention to provide a process for the preparation of alkenoic acid esters comprising contacting a lactone with an alcohol and an acidic catalyst in the gas phase which results in a lower selectivity towards the production of dialkyl ethers.

In a first aspect, the invention provides a process for the preparation of alkenoic acid esters comprising contacting a lactone with an alcohol and an acidic catalyst in the gas phase, characterised in that the process is carried out in the presence of at least 0.26 wt. % water, relative to the amount of the lactone.

The inventors have surprisingly found that with the process according to the first aspect of the invention good production yield and selectivity with respect to the production of alkenoic acid esters from lactone may be achieved. They have also found that with said process the formation of dialkylethers may be advantageously less as compared to converting lactones to alkenoic acid esters when the amount of water is less than 0.26% wt.

DETAILED DESCRIPTION OF A PREFERRED EMBODIMENT

The amount of water, if any, in the processes of U.S. Pat. No. 5,144,061 and U.S. Pat. No. 4,740,613 is not disclosed. However, both publications are silent as to the amount of dialkyl ethers formed. According to U.S. Pat. No. 5,144,061 the starting material can be diluted with an inert gas such as steam. However, the amount of water represented by the steam is not disclosed. Moreover, the steam is referred to as an "inert gas", suggesting that it has no effect in the conversion of lactones to alkenoic acid esters, let alone that it may reduce the formation of dialkyl ethers. Interestingly, in U.S. Pat. No. 5,144,061 it is stated when an acidic catalyst is used, the lactone is preferentially cleaved to alkenecarboxylic ester as compared to the formation of ethers. The inventors of the present invention have nevertheless found that the formation of dialkyl ethers is unsatisfactorily high when the amount of water is less than 0.26 wt %, relative to the amount of the lactone.

Interestingly, the fact that contacting a lactone with an alkanol and an acidic catalyst in the presence of at least 0.26 wt % of water relative to the amount of the lactone may result in less formation of dialkyl ether is all the more surprising since this conversion also involves the production of water (one equivalent with respect to the alkenoic acid esters formed) Nevertheless, it appears that this water which is formed during the course of the reaction does not impart the same effect with respect to amount of dialkyl ether formation or yield or selectivity of alkenoic acid ester formation as does the initial presence of at least 0.26 wt % water, i.e. the initial presence of at least 0.26 wt % water in the process is essential. Therefore, in the context of the invention "the presence to at least 0.26 wt % of water" is understood to refer to the initial presence of 0.26 wt % water relative to the amount of the lactone prior to the start of the reaction, when no or hardly any lactone and/or alkanol has been converted.

Little production of dialkyl ethers may be advantageous because the recovery of the alkenoic acid ester may be easier or less expensive or may require less trained personnel. Also, it may result in the production of a purer alkenoic acid ester. Moreover, it may result in a more optimal use of the substrate lactone and less usage of alkanol, meaning lower costs. The process of the first aspect of the invention has good selectivity and productivity towards the formation of alkenoic acid esters. Preferably said selectivity and yield towards the formation of alkenoic acid esters is equal or even better than those of processes known in the art. The improved yield advantageously allows energy conservation.

The amount of water in the process of the first aspect of the invention is preferably at least 0.26% wt, more preferably at least 0.28% wt, at least 0.5% wt, at least 1% wt, even more preferably at least 1.1% wt, at least 1.2% wt, even more preferably at least 2% wt, 2.2% wt, 2.4% wt, at least 2.5% wt, even more preferably at least 4.5% wt, even more preferably at least 5% wt all relative to the amount of the lactone. The amount of water is preferably 10% wt or less, more preferably 8% wt or less, even more preferably 5% wt or less, all relative to the amount of the lactone.

In an embodiment the amount of water in the process is between 0.26% and 10% wt relative to the amount of the lactone. If the amount of water is too high, e.g. 10% or more, the selectivity towards the production of alkenoic acid ester may become too low and/or the conversion rate (TON) may become too low. Preferably the amount of water in the process of the first aspect of the invention is between 1 and 10% wt, even more preferably between 1 and 5% wt, even more preferably between 1 and 2.5% wt.

An amount of at least 0.26% wt water in the process of the first aspect of the invention can be achieved in many ways.

In one embodiment the presence of at least 0.26 wt % water may be achieved without adding any additional water. For example, the components of the process of the invention (comprising the lactone, alkanol, and acidic catalyst, hereafter referred to as "reaction components") may comprise water. The skilled person can readily determine the water content of said reaction components, for example using Karl Fischer titration, and calculate the amount of water in the process after said reaction components are added to the process before any conversion has taken place. If the resulting amount of water in the process is too low or too high, the skilled person may analyse the water content of reaction components from other batches of from other suppliers etc and select suitable batches such that after adding these to the process the resulting amount of water is not too low or too high.

If, after determining the water content of the reaction components and calculating the theoretical water content of the process after adding said components, the skilled persons finds that the amount of water in the process would be too high, said one or more components may be dried before adding these to the process.

In an embodiment the process according to the first aspect of the invention further comprises adding water. The water may be added to the process in any conceivable way. If, for example, after determining the water content of the reaction components and calculating the theoretical water content of the process after adding said components, the skilled persons finds that the resulting water content would be too low (i.e. less than 0.26% wt) the skilled person may add water to one or more of said reaction components to an extent that the resulting amount of water in the process will be at least 0.26% wt.

In one embodiment the water is added separately, i.e. water is added in addition to the other reaction components. The reaction components and the separately added water may be added to the process in any order. For example, the water may be added before adding the reaction components, or adding one of the reaction components but before adding the other reaction components etc, or at the end, or anywhere in-between, as along adding the water results in the initial presence of at least 0.26% wt water. The water may be added as liquid water. As the reaction proceeds in the gas phase the water may also be added as steam. Of course when in the context of the invention it is referred to that the "water is added separately" this does not necessarily mean that the reaction components do not comprise any water. If the reaction components do not comprise any water it follows that the water should be added separately. If, on the other hand, the reaction components do comprise water but, after determining the water content of the reaction components and calculating the theoretical water content of the process after adding said components, the skilled persons finds that the resulting water content would be less than 0.26% wt, then additional water may be added separately such that the resulting amount of water is at least 0.26% wt.

Acidic catalysts are well known to the skilled person and are commercially available. Examples of suitable acidic catalysts are acidic oxides of elements of main groups III and IV and subgroups IV and VI of the periodic table, such as silica in the form of silica gel, kieselguhr or quartz, as well as phosphorus pentoxide and alumina.

Also acidic zeolites which are crystalline aluminosilicates e.g. of the ZSM types, for example ZSM-5 and aluminium phosphate catalysts or amorphous Silica/Alumina catalysts, e.g. Davicat Sial 3501 (Grace Co.) may be used.

In an embodiment the acidic catalyst is an acidic zeolite catalyst.

The process according to the invention is in general carried out under the following conditions: The molar ratio of lactone to alcohol advantageously ranges from 1:0.5 to 1:10, in particular from 1:1 to 5. In the reaction, a temperature of from 50° C. to 450° C. is maintained. Advantageously, a temperature of from 150° C. to 400° C., in particular from 200° C. to 350° C., is maintained. In general, the reaction is carried out under a pressure from 0.1 to 100 bar, in particular from 0.5 to 10 bar. The weight hourly space velocity through the catalyst is advantageously maintained in the range from 0.1 to 20 g, in particular from 0.1 to 5 g of lactone per g catalyst per hour.

In one embodiment the alkenoic acid ester is pentenoic acid ester.

The alkanol preferably has one, two, or three carbon atoms and is preferably unbranched. Suitable alkanols are methanol, ethanol and propanol. A preferred alkanol is methanol.

In yet another, highly preferred embodiment the alkanol is methanol and the lactone is 5-methylbutyrolactone (γ-valerolactone), thereby forming pentenoic acid methyl ester. Pentenoic acid methyl ester is an important intermediate in the production of adipic acid from renewable sources. Adipic acid itself is an intermediate in the production of 6,6 polyamide (nylon). The most important process to produce adipic acid is based on oil and starts from benzene. In this process benzene is hydrogenated to cyclohexane. Cyclohexane is then oxidised using HNO3 as oxidant to adipic acid. A disadvantage of this process is that it is based on fossil derived oil. Another disadvantage is the evolution of NOx during the oxidations step, which either is vented to the air, which is highly undesirable as it is a greenhouse gas, or is catalytically destroyed, which is an expensive process. New processes for the production of adipic acid have been developed based on butadiene, which is converted tot methyl 3-pentenoate. The next step is isomerisation of methyl 3-pentenoate to methyl 4-pentenoate which can be converted to dimethyladipate. A disadvantage of the butadiene-based processes is the high cost of butadiene. A second disadvantage is the low rate of the methoxycarbonylation of butadiene. Another process for the production of adipic acid starts from levulinic acid as a renewable source. Levulinic acid may be produced from agricultural waste products or waste from the paper industry or municipal waste and therefore constitutes a renewable source of a C-5 fragment. The hydrogenation of levulinic acid has been described and produces valerolactone in high yield.

In an embodiment the 5-methylbutyrolactone is produced by converting levulinic acid to 5-methylbutyrolactone in a hydrogenation reaction. Such processes are for example described in L. E. Manzer, Appl. Catal. A, 2004, 272, 249-256; J. P. Lange, J. Z. Vestering and R. J. Haan, Chem. Commun., 2007, 3488-3490; R. A. Bourne, J. G. Stevens, J. Ke and M. Poliakoff, Chem. Commun., 2007, 4632-4634; H. S. Broadbent, G. C. Campbell, W. J. Bartley and J. H. Johnson, J. Org. Chem., 1959, 24, 1847-1854; R. V. Christian, H. D. Brown and R. M. Hixon, J. Am. Chem. Soc., 1947, 69, 1961-1963; L. P. Kyrides and J. K. Craver, U.S. Pat. No.

2,368,366, 1945; H. A. Schuette and R. W. Thomas, J. Am. Chem. Soc., 1930, 52, 3010-3012.

In another embodiment the levulinic acid is prepared by converting a C6 carbohydrate to levulinic acid in an acid-catalysed reaction. Such processes are for example described in L. J. Carlson, U.S. Pat. No. 3,065,263, 1962; B. Girisuta, L. P. B. M. Janssen and H. J. Heeres, Chem. Eng. Res. Des., 2006, 84, 339-349; B. F. M. Kuster and H. S. Vanderbaan, Carbohydr. Res., 1977, 54, 165-176; S. W. Fitzpatrick, WO8910362, 1989, to Biofine Incorporated; S. W. Fitzpatrick, WO9640609 1996, to Biofine Incorporated. Examples of C6 carbohydrates are glucose, fructose, mannose and galactose. Preferred raw material for the C6 carbohydrates is lignocellulosic material containing carbohydrate based polymers composed partly or entirely from C6 sugars such as cellulose, starch and hemicellulose. The C6 carbohydrate may comprise other components, such as plant waste, paper waste, sewage etc.

In another aspect the invention provides a process to produce adipic acid dimethyl ester comprising converting the pentenoic acid methyl ester produced in the process of the first aspect of the invention to adipic acid dimethyl ester in a carbonylation reaction in the presence of CO and methanol. Such carbonylation processes are well known in the art and are described e.g. in WO2001068583.

In a further aspect the invention provides a process to produce adipic acid comprising converting the adipic acid dimethyl ester produced in the second aspect of the invention in a hydrolysis reaction. The process to produce adipic acid according to the third aspect of the invention advantageously allows the use of renewable sources such as plant waste, sewage waste etceteras instead of using fossil sources.

The invention will be further elucidated with reference to the following examples, without however being limited thereto.

LHSV=Liquid Hourly Space Velocity=ml of feed/ml of catalyst·hour.

WHS=Weight Hourly Space Velocity=grams of feed/gram of catalyst·hour.

Davicat Sial 3501, an amorphic acidic, non-zeolytic catalyst was obtained from Grace Davison, Specialty Catalysts & Process Technologies, 7500 Grace Dr, Columbia, MD2 1042, USA. Zeolyst CBV2314CY, an acidic, zeolytic catalyst, was obtained from Zeolyst International, P.O. Box 830, Valley Forge, Pa. 19482 USA. Water content was determined by Karl Fischer titration. Valerolactone and methanol were obtained from Aldrich Co.

Example 1

A tubular reactor (total length, 0.47 m; total volume, 120 mL; having an upper and lower section each having a diameter of 12.7 mm, a length of 4 cm, and a volume of 15 mL; and having an intermediate heated section having a diameter of 20 mm and a volume of 105 mL) was filled with 50 ml of Davicat Sial 3501. A gaseous mixture of methanol, γ-valerolacton and N2 (5 Nl/hr) was passed over this catalyst. The temperature of the catalyst bed was 255° C. SV: 0.26; WHSV: 0.63; molar ratio methanol:valerolactone=3:1.

Different amounts of water were separately added to the reaction mixture. After addition of the water, but before the start of the reaction, the total amount of water in the reaction was measured by Karl Fischer titration. During approximately 1400 minutes the amounts of valerolactone and dimethyl ether were measured by GC and the selectivities towards formation of pentenoic acid methyl ester based on the initial amount of γ-valerolactone and of formation of dimethyl ether based on the initial amount of methanol were calculated.

TABLE 1

| amount of water in total feed (wt %) | Amount of water w.r.t. valerolacton (wt %) | reaction time (min) | selectivity to pentenoic acid methyl ester (%) | selectivity towards dimethyl ether (%) | Grams of dimethyl ether/kg of methyl-pentenoate |
|---|---|---|---|---|---|
| 0.13 | 0.26 | 1430 | 98.6 | 52.7 | 225 |
| 1.1 | 2.2 | 1400 | 100 | 43.5 | 155 |
| 2.5 | 5.0 | 1425 | 99.1 | 38.7 | 128 |
| 9.9 | 21.1 | 1425 | 94.0 | 39.3 | 131 |

Example 2

A tubular reactor as in Example 1 was filled with 50 ml of Zeolyst CBV2314 CY (Zeolite ZSM-5 extrudate). A gaseous mixture of methanol, γ-valerolacton and N2 (5 Nl/hr) was passed over this catalyst. The temperature of the catalyst bed was 255° C.

Zeolyst CBC2314CY, an acidic, zeolytic catalyst, was obtained from Zeolyst International, P.O. Box 830, Valley Forge, Pa. 19842 USA. Molar ratio methanol:valerolactone=3:1; LHSV, 0.26; WHSV, 0.4. Different amounts of water were separately added to the reaction. After addition of the water, but before the start of the reaction, the total amount of water in the reaction was measured by Karl Fischer titration.

TABLE 2

| amount of water in total feed (wt %) | Amount of water w.r.t. valerolactone (wt %) | reaction time (min) | selectivity to pentenoic acid methyl ester (%) | selectivity to dimethyl ether (%) | Grams of dimethyl ether/kg of methyl-pentenoates |
|---|---|---|---|---|---|
| 0.14 | 0.28 | 1390 | 96.2 | 67.5 | 418 |
| 1.2 | 2.4 | 1635 | 94.6 | 60.8 | 313 |
| 4.6 | 9.3 | 1400 | 93.0 | 58.0 | 278 |

The invention claimed is:

1. A process for preparing an alkenoic acid ester comprising contacting a lactone with an alcohol and an acidic zeolytic catalyst in gas phase, wherein said process is carried out in the presence of at least 0.26 wt. % water, relative to amount of the lactone.

2. The process according to claim 1, wherein said amount of water in the process is from 0.26% to 10% wt water relative to the amount of said lactone.

3. The process according to claim 1, further comprising adding water.

4. The process according to claim 3, wherein said water is added separately.

5. The process according to claim 1, wherein said alkenoic acid ester is pentenoic acid ester.

6. A process according to claim 1, wherein the alcohol is methanol.

7. The process according to claim 5, wherein said alcohol is methanol and wherein the lactone is 5-methylbutyrolactone, thereby forming pentenoic acid methyl ester.

8. The process according to claim 7, wherein said 5-methylbutyrolactone is produced by converting levulinic acid to 5-methylbutyrolactone in a hydrogenation reaction.

9. The process according to claim 8, wherein said levulinic acid is prepared by converting a C6 carbohydrate to levulinic acid in an acid-catalysed reaction.

10. A process for producing adipic acid dimethyl ester comprising converting the pentenoic acid methyl ester produced according to claim 7, to adipic acid dimethyl ester in a carbonylation reaction in the presence of CO and methanol.

11. A process for producing adipic acid comprising converting the adipic acid dimethyl ester produced according to claim 10, in a hydrolysis reaction.

12. The process of claim 1, wherein said process is carried out at a temperature of from 150° C. to 400° C.

13. The process of claim 1, wherein said process is carried out at a temperature of from 200° C. to 300° C.

14. The process according to claim 1, wherein said amount of water in the process is from 0.5% to 10% wt water relative to the amount of said lactone.

15. The process according to claim 1, wherein said amount of water in the process is from 1% to 8% wt water relative to the amount of said lactone.

16. A process for preparing a pentenoic acid methyl ester comprising contacting 5-methylbutyrolactone with methanol and an acidic zeolytic catalyst in gas phase at a temperature of from 150° C. to 400° C., wherein said process is carried out in the presence of at least 0.26 wt. % water, relative to amount of the 5-methylbutyrolactone.

\* \* \* \* \*